United States Patent [19]

Grindey et al.

[11] Patent Number: 5,217,974

[45] Date of Patent: Jun. 8, 1993

[54] METHOD FOR TREATING GAR-TRANSFORMYLASE TUMORS IN MAMMALS AND REDUCING MAMMALIAN TOXICITY

[75] Inventors: Gerald B. Grindey, Indianapolis; Chuan Shih, Carmel, both of Ind.

[73] Assignee: Eli Lilly and Company, Indianapolis, Ind.

[21] Appl. No.: 940,568

[22] Filed: Sep. 4, 1992

Related U.S. Application Data

[63] Continuation of Ser. No. 911,429, Jul. 10, 1992, abandoned, which is a continuation of Ser. No. 750,841, Aug. 26, 1991, abandoned, which is a continuation-in-part of Ser. No. 677,031, Mar. 29, 1991, abandoned.

[51] Int. Cl.$^5$ ............... A01N 43/40; A01N 43/54; A61K 31/44; A61K 31/505
[52] U.S. Cl. .................. 514/260; 514/340; 514/227.2; 514/267; 514/269; 514/275; 514/292; 514/293; 514/342; 514/443; 514/445; 514/468
[58] Field of Search ............ 514/260, 340, 227.2, 514/267, 269, 275, 292, 293, 342, 443, 445, 468

[56] References Cited

U.S. PATENT DOCUMENTS

| | | | |
|---|---|---|---|
| 4,684,653 | 8/1987 | Taylor et al. | 514/258 |
| 4,833,145 | 5/1989 | Taylor et al. | 514/258 |
| 4,871,743 | 10/1989 | Taylor et al. | 515/272 |
| 4,882,334 | 11/1989 | Shih et al. | 514/258 |
| 4,902,796 | 2/1990 | Taylor et al. | 544/279 |
| 4,946,846 | 8/1990 | Nomura et al. | 544/258 |
| 4,996,206 | 2/1991 | Taylor et al. | 514/258 |
| 4,997,838 | 3/1991 | Akimoto et al. | 514/258 |
| 5,010,194 | 4/1991 | Mueller et al. | 544/258 |

FOREIGN PATENT DOCUMENTS

| | | |
|---|---|---|
| 1093554 | 1/1981 | Canada . |
| 409125 | 1/1991 | European Pat. Off. . |
| 88/08844 | 11/1988 | PCT Int'l Appl. . |

OTHER PUBLICATIONS

Young, et al., *Proc. Amer. Assoc. Cancer Res.*, 31, 1053 (1990).
Muggia, et al., *Proc. Amer. Soc. Clinical Oncology*, 1, 1285 (1990).
Grindey, et al., Proceedings of the 82nd Annual Meeting of the American Association for Cancer Research, vol. 32, p. 384, Abst. 1921 (1991).
Internal Eli Lilly and Company Memo Entitled "Cancer Progress Conference Trip Report".
Derwent Abstract 45319S (abstracting DT2063027).
Morgan, S. L., et al., *Arthritis and Rheumatism* 33: 9–18 (1990).
Straw, et al., *Cancer Research*, 44:3114–3119 (1984).
Temple, et al., *Cancer Treatment Reports*, 65:1117–1119 (1981).

*Primary Examiner*—Nathan M. Nutter
*Attorney, Agent, or Firm*—Steven A. Fontana; Leroy Whitaker

[57] ABSTRACT

Administration of a folate binding protein binding agent in conjunction with use of an antitumor agent which is an inhibitor of glycinamide ribonucleotide transformylase or other antifolate reduces the toxic effects of such agent and provides an enhanced therapeutic index.

22 Claims, No Drawings

METHOD FOR TREATING GAR-TRANSFORMYLASE TUMORS IN MAMMALS AND REDUCING MAMMALIAN TOXICITY

This application is a continuation of application Ser. No. 07/911,429 filed Jul. 10, 1992, now abandoned, which is a continuation application Ser. No. 07/750,841, filed Aug. 26, 1991, now abandoned, which is a continuation-in-part of application Ser. No. 07/677,031 filed Mar. 29, 1991 and now abandoned.

BACKGROUND OF THE INVENTION

Lometrexol is the generic name given to 5,10-dideazatetrahydrofolic acid, also referred to as DDATHF. Lometrexol is a member of a new class of antitumor agents which have been found to specifically inhibit glycinamide ribonucleotide (GAR) transformylase, an enzyme required in the initial stages of purine biosynthesis, see *J. Med. Chem.*, 28, 914 (1985). Several of these GAR-transformylase inhibitors are described, along with their antitumor utilities, by Taylor et al. in U.S. Pat. Nos. 4,684,653, 4,833,145, 4,902,796, 4,871,743 and 4,882,334. GAR-transformylase inhibitors are also known to be useful in treating conditions such as gout, psoriasis, mycosis fungoides, autoimmune disorders, rheumatoid arthritis and other inflammatory disorders, and during organ transplantation and other related immunosuppressant related conditions.

Lometrexol has been studied clinically and shown to be a potent antitumor agent, especially against solid tumors such as colorectal, lung, breast, head and neck and pancreatic; Young et al., *Proc. Amer. Assoc. Cancer Research,* 31, 1053 (1990). Like most other antitumor agents, Lometrexol exhibits some undesirable side effects, in addition to its efficacy against tumors; Muggia et al., *Proc. Amer. Soc. Clinical Oncology,* 9, 1285 (1990). Typical side effects observed to date include anorexia, weight loss, mucositis, leukopenia, anemia, hypoactivity and dehydration.

We have now discovered that the toxic effects of lometrexol and related GAR-transformylase inhibitors and other antifolate agents which bind to folate binding protein (FBP) (see, e.g., Kane, et al., *Laboratory Investigation,* 60, 737 (1989)) can be significantly reduced by the presence of a FBP binding agent, without adversely affecting therapeutic efficacy. The present invention thus provides a method for improving the therapeutic utility of GAR-transformylase inhibitors and other antifolates by co-administering a FBP binding agent to the host under going treatment.

SUMMARY OF THE INVENTION

In one aspect of this invention, we provide a method of inhibiting the growth of GAR-transformylase-dependent tumors in mammals comprising administering to said mammals an effective amount of a GAR-transformylase inhibitor or other antifolate which binds to a FBP in combination with a toxicity-reducing amount of a FBP binding agent, or a physiologically-available salt or ester thereof. The invention more particularly provides a method for reducing the mammalian toxicity of a GAR-transformylase inhibitor or other antifolate which binds to a FBP which comprises administering a toxicity-reducing amount of a FBP binding agent or a physiologically-available salt or ester thereof to the mammal receiving treatment. In particular, there is provided a method for reducing the toxicity of a GAR-transformylase inhibitor or other antifolate which binds to a FBP in a mammal which comprises pretreating the mammal with an amount of a compound selected from folic acid, (6R)-5-methyl-5,6,7,8-tetrahydrofolic acid, and (6R)-5-formyl-5,6,7,8-tetrahydrofolic acid, or a physiologically-available salt or ester thereof, sufficient to have substantially blocked the FBP before administration of the antifolate. In the most preferred embodiment of the invention, Lometrexol is administered to a subject suffering from a solid tumor or other type of cancer and in need of treatment after pretreatment with folic acid, thereby reducing toxic effects of Lometrexol while maintaining good antitumor activity.

DETAILED DESCRIPTION OF THE INVENTION

The invention provides a method for reducing the toxicity of GAR-transformylase inhibitor or other antifolates that bind to a FBP that is found in biological systems by the prior administration of a FBP binding agent or a physiologically-available salt or ester thereof. GAR-transformylase inhibitors and related antifolates are those compounds which effectively inhibit the biological actions of the enzyme known as glycinamide ribonucleotide transformylase. This enzyme is well known to be required in the initial stages of purine biosynthesis in mammals, which is implicated in DNA synthesis. Interruption of this biosynthetic pathway causes a disturbance in DNA synthesis and consequently causes cell death. Any compound which is shown to inhibit the GAR-transformylase or other folate-requiring enzyme is subject to treatment in accordance with this invention.

Typical GAR-transformylase inhibitors include the pyrido[2,3-d]pyrimidine derivatives described by Taylor et al. in U.S. Pat. Nos. 4,684,653, 4,833,145, 4,902,796, 4,871,743 and 4,882,334. Another series of GAR-transformylase inhibitors has recently been described by Akimoto in U.S. Pat. No. 4,997,838. Antifolate compounds which can be employed in this invention include thymidylate synthase inhibitors as found in EPO Patent Application 239,362. All of the foregoing references are incorporated herein by reference for their teaching of the structure and synthesis of typical GAR-transformylase inhibitors and antifolates. Other GAR-transformylase inhibitors and antifolates are also included within the scope of this invention, and such compounds can be determined by routine evaluation of either their ability to interact with and inhibit the subject enzyme or to bind to the FBP.

In a preferred embodiment of the invention, folic acid is administered to a subject subsequently receiving an agent defined by the formula

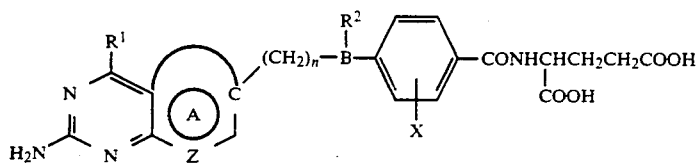

wherein
- R[1] is hydroxy or amino;
- R[2] is hydrogen, methyl, ethyl, or propynyl;
- B is —CH— or —N—;
- n is 1, 2 or 3;
- Z is nitrogen or carbon;
- A is pyrido, tetrahydropyrido, pyrrolo, dihydropyrrolo, cyclopentyl or cyclohexyl;
- X is hydrogen or halo; and pharmaceutically acceptable salts thereof.

In a particularly preferred embodiment of the invention, lometrexol is utilized as the GAR-transformylase inhibitor.

As noted above, the drug products which can be employed in the present invention include other antifolates which are capable of binding to folate binding protein. Folic acid itself has a binding constant (ng/ml) of 1.8, and lometrexol has a binding constant of 9.7 to bovine FBP. Any GAR-transformylase inhibitor or other antifolate that binds at less than about 500 ng/ml can be utilized in the method of this invention. The folate binding constant for drug products can be readily determined by the general procedure of Dunn and Foster, *Clin. Chem.*, 19 (10), 1101–1105 (1973). Typical antifolates evaluated in the referenced procedure have the following folate binding constants presented in Table I below:

TABLE I

| Structure | Binding Constant (ng/ml) |
|---|---|
| n = 3, X = H | 12.5 |
| n = 2, X = 2-F | 14.0 |
| n = 2, X = 3-F | 30.7 |
| (furan derivative) | 250.8 |
| (thiophene derivative) | 24.5 |
| (cyclohexyl-S derivative) | 26.0 |
| (propynyl N-linked derivative) | 12.0 |

TABLE I-continued

| | Binding Constant (ng/ml) |
|---|---|
| 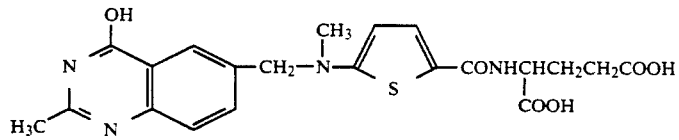 | 245 |

As used in this invention, the term "FBP binding agent" refers to folic acid, (6R)-5-methyl-5,6,7,8-tetrahydrofolic acid, or (6R)-5-formyl-5,6,7,8-tetrahydrofolic acid. This latter compound is the (6R)-isomer of leucovorin as disclosed in *J. Am. Chem. Soc.*, 74, 4215 (1952). Both of the tetrahydrofolic acid compounds are in the unnatural configuration at the 6-position—they are 10–20 fold more efficient in binding the folate binding protein compared with their respective (6S)-isomer—see Ratnam, et. al., Folate and Antifolate Transport in Mammalian Cells Symposium, Mar. 21–22, 1991, Bethesda, Md. These compounds are usually prepared as a mixture with their natural form (6S) of diastereomers by non-stereoselective reduction from the corresponding dehydro precursors followed by separation through chromatographic or enzymatic techniques. See e.g., PCT Patent Application Publication WO 880844 (also Derwent Abstract 88-368464/51) and Canadian Patent 1093554.

Folic acid is a vitamin which is required by mammals for proper regeneration of the blood-forming elements and their functioning, and as a coenzyme is involved in intermediary metabolic processes in which one-carbon units are transferred. These reactions are important in interconversions of various amino acids and in purine and pyrimidine synthesis. Folic acid is commonly supplied to diets of humans via consumption of food sources such as liver, kidney, dry beans, asparagus, mushrooms, broccoli, lettuce, milk and spinach, as well as by vitamin supplements. The minimum amount of folic acid commonly required by normal adults is about 0.05 mg/day. According to this invention, folic acid, or a physiologically-available salt or ester thereof, is administered to a human subject at a dose of about 0.5 mg/day to about 30 mg/day to diminish the toxic effects of a GAR-transformylase inhibitor or other antifolate also being administered to such subject. In a preferred embodiment, folic acid will be administered at about 1 to about 5 mg/day together with the normal dosing of GAR-transformylase inhibitor such as lometrexol.

Based upon the relative binding constants for the respective compounds, it will be expected that approximately 1 mg/day to 90 mg/day (preferably approximately 2-15 mg/day) of (6R)-5-methyl-5,6,7,8-tetrahydrofolic acid or about 5-300 mg/day (preferably about 10-50 mg/day) of (6R)-5-formyl-5,6,7,8-tetrahydrofolic acid, or their respective physiologically-available salt or ester thereof, will be employed with the GAR-transformylase inhibitor.

"Physiologically-available salt" refers to potassium, sodium, lithium, magnesium, or preferably a calcium salt of the FBP binding agent. "Physiologically-available . . . ester" refers to esters which are easily hydrolyzed upon administration to a mammal to provide the corresponding FBP binding agent free acid, such as $C_1$–$C_4$ alkyl esters, mixed anhydrides, and the like.

The FBP binding agent to be utilized according to this invention can be in its free acid form, or can be in the form of a physiologically-acceptable salt or ester which is converted to the parent acid in a biological system. The dosage generally will be provided in the form of a vitamin supplement, namely as a tablet administered orally, preferably as a sustained release formulation, as an aqueous solution added to drinking water, an aqueous parenteral formulation, e.g., an intravenous formulation, or the like.

The FBP binding agent is administered to the subject mammal prior to treatment with the GAR-transformylase inhibitor or other antifolate. Pretreatment with the suitable amount of FBP binding agent from about 1 to about 24 hours is usually sufficient to substantially bind to and block the folate binding protein prior to administration of the GAR-transformylase inhibitor or other antifolate. Although one single dose of the FBP binding agent, preferably an oral administration of folic acid, should be sufficient to load the folate binding protein, multiple dosing of the FBP binding agent can be employed for periods up to weeks before treatment with the active agent to ensure that the folate binding protein is sufficiently bound in order to maximize the benefit derived from such pretreatment.

In the especially preferred embodiment of this invention, about 1 mg to about 5 mg of folic acid is administered orally to a mammal about 1 to about 24 hours prior to the parenteral administration of the amount of lomotrexol which is normally required to attain the desired therapeutic benefit. Although greater or additional doses of folic acid or another FBP binding agent are also operable, the above parameters will usually bind the folate binding protein in an amount sufficient to reduce the toxicity effects normally seen upon lomotrexol administration above.

It should be noted that the FBP binding agent is not an antitumor agent and that the pretreatment of a mammal with a FBP binding agent is not a synergistic or potentiating effect. Rather, by having substantially bound the folate binding protein with a FBP binding agent prior to administration of the GAR-transformylase inhibitor or other antifolate, the toxic effects of such subsequent treatment are greatly reduced without affecting the therapeutic efficacy.

The effect of folic acid on GAR-transformylase inhibitors has been demonstrated in standard tests commonly utilized to determine the antitumor activity and toxic effects of the GAR-transformylase inhibitors themselves. In one such test, mice are inoculated with the C3H strain of mammary adenocarcinoma by inserting a 2 mm by 2 mm section of tumor into the axillary region of the mice by trocar. In all experiments, lometrexol was administered intraperitoneally once a day for five consecutive days, starting on the day following tumor implantation. Ten animals were used at each dosage level. Antitumor activity was assessed on day ten by measuring the length and width of the tumor growth using vernier calipers, and the activity was expressed as a percent inhibition of tumor growth.

When lometrexol was administered to infected mice which are maintained on a diet totally free of folic acid for two weeks prior to and during treatment, it exhibited moderate antitumor activity at very low doses, but also caused severe toxicity at a very low dose (measured as death of mice). These data are presented in Table II below.

TABLE II

Antitumor Activity and Toxicity of Lometrexol in C3H Mice after Two Weeks on Folate-Free Diet

| Lometrexol Dose (mg/kg) | Antitumor Activity (% Inhibition) | Toxicity (Mice Dead/Total Mice) |
|---|---|---|
| 0.0625 | 0% | 0/10 |
| 0.125 | 0% | 0/10 |
| 0.25 | 21% | 0/10 |
| 0.5 | 88% | 0/10 |
| 1.0 | 100% | 8/10 |

A test group of mice were maintained on a folic acid free diet for two weeks before treatment. Folic acid was then administered during the treatment by providing the animals drinking water containing 0.0003% folic acid (weight/volume). This concentration translates to about 1.75 mg of folic acid per square meter of body surface per day, since the animals consume about 4 ml of water each day.

$$\frac{0.0003 \text{ grams}}{100 \text{ ml.}} \times \frac{4 \text{ ml.}}{\text{day}} = \frac{0.000012 \text{ grams}}{\text{day}} = \frac{0.012 \text{ milligrams}}{\text{day}}$$

The average size of a mouse is $0.00687 \text{ m}^2$ $$\frac{0.012 \text{ grams}}{\text{day}} \times \frac{1}{0.00687 \text{ m}^2} = 1.75 \text{ mg/m}^2/\text{day}$$

For a human subject of about $1.73 \text{ m}^2$ size, this translates to an adult human dosage of about 3.0 mg/day. The effect of the foregoing folate dosage on the activity and toxicity of lometrexol is shown in Table III below:

TABLE III

Antitumor Activity and Toxicity of Lometrexol in C3H Mice after Two Weeks on Folate-Free Diet Plus Addition of 0.0003% Folate to Drinking Water

| Lometrexol Dose (mg/kg) | Antitumor Activity (% Inhibition) | Toxicity (Mice Dead/Total Mice) |
|---|---|---|
| 0.125 | 13% | 0/10 |
| 0.25 | 26% | 0/10 |
| 0.5 | 48% | 0/10 |
| 1.0 | 97% | 0/10 |
| 2.0 | 98% | 0/10 |
| 4.0 | 99% | 4/10 |

As the foregoing results indicate, addition of the indicated level of folic acid to the diet of a subject receiving lometrexol results in excellent antitumor activity at low doses, with little or no toxic effects.

Larger doses of folic acid appear to have an even more dramatic effect on the antitumor activity and toxicity of the GAR-transformylase inhibitor. For example, when mice were maintained on a folate acid-free diet for two weeks before treatment with lometrexol, and then given water containing 0.003% (weight/volume) of folic acid (which translates to an adult human dose of about 30 mg/day), good antitumor activity of lometrexol is observed at higher dose levels. These results are shown in Table IV below:

TABLE IV

Antitumor Activity and Toxicity of Lometrexol in C3H Mice after Two Weeks on Folate-Free Diet Plus Addition of 0.003% Folate to Drinking Water

| Lometrexol Dose (mg/kg) | Antitumor Activity (% Inhibition) | Toxicity (Mice Dead/Total Mice) |
|---|---|---|
| 6.25 | 91% | 0/10 |
| 12.5 | 89% | 0/10 |
| 25 | 97% | 0/10 |
| 50 | 96% | 0/10 |

The foregoing data establish that for tumor bearing mice maintained on a folic acid free diet prior to and during treatment with lometrexol, the toxicity of lometrexol is very large, with 1 mg/kg/day being lethal to the majority of the mice, and lower antitumor activity is observed at non-toxic drug doses. Very low doses of folic acid (about 1 to 2 mg/day for an adult human) partially reversed drug toxicity and improved antitumor activity. Larger doses of folic acid (up to about 30 mg/day for an adult human) dramatically reduced lometrexol toxicity and markedly improved antitumor activity. Thus, the use of folic acid in combination with a GAR-transformylase inhibitor markedly reduces drug toxicity without adversely affecting antitumor activity.

In a typical clinical evaluation involving cancer patients, all of whom have histologically or cytologically confirmed diagnosis of cancer, lometrexol is administered in combination with folic acid. Lometrexol is administered in four doses over a two week period by rapid intravenous injection, followed by two weeks of non-therapy. Dosing is made on days 1, 4, 8 and 11 of any two week period. Patients will have an initial course of therapy at a dose of 5 mg/m$^2$/dose, and depending upon the toxic effects observed in the initial course, their subsequent courses may be at the same dose, or may be escalated to 6 mg/m$^2$, or may be attenuated to 4 mg/m$^2$.

These patients will also receive orally 1 mg/day of folic acid, beginning the day before they are started on the first course of lometrexol, and continuing throughout their exposure to the drug. Such dosage of folic acid will be given once daily, generally in the morning hours.

In preparation for the foregoing clinical study, pilot studies in humans have established that folic acid given to patients receiving lometrexol has effected reduced side effects due to the lometrexol. Specifically, in one subject who had a nasalpharyngeal carcinoma, who was supplimented with folic acid at 0.5 to 1.0 mg/day, lometrexol was well tolerated for up to 12 months of therapy. Moreover, this patient has no clinical evidence of disease after the 12 months of therapy. These data are consistent with the animal studies reported above.

We claim:

1. A method of inhibiting the growth of GAR-transformylase-dependent tumors in mammals comprising administering to said mammals an effective amount of a GAR-transformylase inhibitor which binds to a folate binding protein in combination with a toxicity-reducing amount of a folate binding protein binding agent selected from folic acid, (6R)-5-methyl-5,6,7,8-tetrahydrofolic acid, and (6R)-5-formyl-5,6,7,8-tetrahydrofolic acid, or a physiologically-available salt or ester thereof.

2. The method of claim 1 wherein the GAR-transformylase inhibitor is a pyrido[2,3-d]pyrimidine.

3. The method of claim 2 wherein the GAR-transformylase inhibitor is lometrexol.

4. The method of claim 1 wherein the folate binding protein binding agent is folic acid.

5. The method of claim 3 wherein the folate binding protein binding agent is folic acid.

6. The method of claim 5 wherein the folic acid is administered at a dose of about 0.5 mg/day to about 30 mg/day.

7. The method of claim 5 wherein the folic acid is administered at a dose of about 1 mg/day to about 5 mg/day.

8. A method for reducing mammalian toxicity of a GAR-transformylase inhibitor which binds to a folate binding protein consisting of administering a toxicity reducing amount of a folate binding protein binding agent selected from folic acid, (6R)-5-methyl-5,6,7,8-tetrahydrofolic acid, and (6R)-5-formyl-5,6,7,8-tetrahydrofolic acid, or a physiologically-available salt or ester thereof, to the mammal receiving treatment with the GAR-transformylase inhibitor.

9. The method of claim 8 wherein the GAR-transformylase inhibitor is a pyrido[2,3-d]pyrimidine.

10. The method of claim 9 wherein the GAR-transformylase inhibitor is lometrexol.

11. The method of claim 8 wherein the folate binding protein binding agent is folic acid.

12. The method of claim 11 wherein folic acid is administered at a dose of about 0.5 mg/day to about 30 mg/day.

13. The method of claim 12 wherein folic acid is administered at a dose of about 1 mg/day to about 5 mg/day.

14. The method of claim 8 wherein the folate binding protein binding agent is (6R)-5-methyl-5,6,7,8-tetrahydrofolic acid or a physiologically-available salt or ester thereof.

15. The method of claim 8 wherein the folate binding protein binding agent is (6R)-5-formyl-5,6,7,8-tetrahydrofolic acid or a physiologically-available salt or ester thereof.

16. A method for reducing the toxicity of a GAR-transformylase inhibitor or other antifolate which binds to a folate binding protein in a mammal which comprises pretreating the mammal with an amount of a folate binding protein binding agent selected from folic acid, (6R)-5-methyl-5,6,7,8-tetrahydrofolic acid, and (6R)-5-formyl-5,6,7,8-tetrahydrofolic acid, or a physiologically available salt or ester thereof, sufficient to have substantially blocked the folate binding protein before administration of the antifolate.

17. The method of claim 16 wherein the GAR-transformylase inhibitor is lomotrexol.

18. The method of claim 16 wherein the folate binding protein binding agent is folic acid.

19. The method of claim 18 wherein the folic acid is administered about 1 to about 24 hours prior to administration of the antifolate.

20. The method of claim 19 wherein a dose of about 0.5 mg to about 30 mg of folic acid is administered.

21. The method of claim 10 wherein the folate binding protein binding agent is folic acid, or a physiologically-available salt or ester thereof.

22. The method of claim 17 wherein the folate binding protein binding agent is folic acid, or a physiologically-available salt or ester thereof.

* * * * *